United States Patent
Barak

(10) Patent No.: US 7,163,381 B1
(45) Date of Patent: Jan. 16, 2007

(54) PUMP AND METHOD OF PUMP CONTROL

(75) Inventor: Swi Barak, Caesarea (IL)

(73) Assignee: Caesarea Medical Electronics, Caesarea Industrial Park (IL)

( * ) Notice: Subject to any disclaimer, the term of this patent is extended or adjusted under 35 U.S.C. 154(b) by 505 days.

(21) Appl. No.: 10/604,522

(22) Filed: Jul. 28, 2003

Related U.S. Application Data

(60) Provisional application No. 60/489,775, filed on Jul. 24, 2003.

(51) Int. Cl.
*F04B 49/00* (2006.01)
*H02H 7/085* (2006.01)

(52) U.S. Cl. .................... 417/44.11; 318/476
(58) Field of Classification Search ............... 318/476, 318/477; 417/44.1, 44.11, 412, 474
See application file for complete search history.

(56) References Cited

U.S. PATENT DOCUMENTS 3,379,950 A * 4/1968 Friedline ................... 318/477
4,322,668 A * 3/1982 Trussler et al. ............ 318/476
6,267,559 B1 * 7/2001 Mossman et al. ......... 417/44.1

* cited by examiner

*Primary Examiner*—Michael Koczo, Jr.
(74) *Attorney, Agent, or Firm*—Gregory Bradley; Jill Denesvich; Henry E. Bartony, Jr.

(57) ABSTRACT

A pump includes a motor and a motor control in operative connection with the motor. The motor control provides energy input to the motor to drive the motor and receives feedback from the motor of motor function. The motor control includes a motor control protocol that controls the energy input to the motor based upon the feedback received from the motor. The motor control protocol causes a rapid increase in energy provided to the motor if motor feedback indicates an unusual load on the motor.

13 Claims, 6 Drawing Sheets

PUMP AND METHOD OF PUMP CONTROL

CROSS-REFERENCE TO RELATED APPLICATION

This application claims priority to U.S. Provisional Patent Application Ser. No. 60/489,775 filed on Jul. 24, 2003, the disclosure of which is incorporated herein by reference.

BACKGROUND OF THE INVENTION

This invention relates to pumps and to methods of pump control, and particularly, to a piston pump for administering liquids to a patient through a flexible tube and to a method of control of such a piston pump.

Systems for administering liquids to a patient are widely known. However, a variety of different pumps are available for propelling a liquid to a patient, which may differ, among others, in the manner and the principle in which they operate.

The present invention is concerned, in preferred embodiments, with two aspects of a system for administering a liquid to a patient. In a first aspect, the invention provides a pumping mechanism for a pump of the aforementioned type. In a second aspect, the invention provides a method of control of a liquid administering pump.

SUMMARY OF THE INVENTION

The invention provides, by a first of its aspects, a piston pump for propelling liquid through a lumen of a flexible tube segment. The pump includes a first tube-clamping member, a first set of tube squeezing members, a second tube clamping member and a second set of tube squeezing members. The members are preferably arranged in a direction from upstream to downstream. Further, the pump includes a synchronizing arrangement for activating the members in a sequential order such that fluid in the tube is displaced in a downstream direction.

The sequential activating order of the elements ensures continuous and repeatable operation of the pump, and comprises the following steps:

(a) activating the second tube-clamping member into blocking the tube's lumen and the first tube-clamping member to open the tube's lumen;

(b) activating the second set of tube squeezing members to constrict the respective tube portion and the first set of tube squeezing members to allow expansion of the respective tube portion;

(c) activating the first tube-clamping member into blocking the tube's lumen;

(d) activating the second clamping member to open the tube's lumen, and the second set of tube squeezing members to allow expansion of the respective tube portion; and (e) activating the first set of tube squeezing members to constrict the respective tube portion.

It will be noted, however, that the alphabetic characters used to designate the steps are provided for convenience only and do not imply any particular order of performing the steps.

According to one preferred embodiment of the invention, the first clamping member, the second clamping member and squeezing members of the first and second set are axially displaced along an axis normal to a longitudinal axis of the lumen between an open and a blocked position. Optionally, the pressing surface of the squeezing members can be either flat or designed shaped for designed squeezing.

According to still a preferred embodiment, the sectional area of the first set of squeezing members is about twice that of the second set of squeezing members. By an improved design of the pump, there is further provided a counter member associated with a door of the pump, wherein the first and second tube-clamping members clamp the tube against the counter member. Further, the pump includes a flexible cradle associated at least with the first and second tube-squeezing member. The flexible cradle supports the tube at least at the expanded position. At the expanded position of the first and second tube squeezing members, the tube is pressed between the cradle and the first and second tube squeezing members so as to assume its shape.

The synchronizing arrangement preferably comprises a cam and follower mechanism associated with each of the members, and a revolving axle extending parallel to the tube's lumen. According to one possible arrangement, there are a number of eccentric members mounted on the axle. The eccentric members are operable to engage the tube clamping and the tube squeezing members, respectively, for imparting reciprocal axial displacement to them in a direction normal to the longitudinal axis. Preferably, the eccentric members are normally biased to engage the tube.

By another preferred embodiment, the present invention includes a disposal flow set including a drip chamber, an administration tube, a valve and a number of squeezing segments. Each squeezing segment preferably includes a stopper in each end. The stoppers are used for locating the segment in the pumping unit. When a segment loses its flexibility, another segment can be used.

By another preferred embodiment, the present invention includes a motor for rotating the axis on which the cams are located.

According to a second aspect of the present invention, there is provided a motor and a micro-controller to control motor revolutions in order to achieve an improved linear delivery of the liquid and to prevent pulsation effects. The micro-controller controls motor revolutions by using the following algorithm:

(a) the motor revolution is divided into a number of steps;

(b) a controller rotates the motor, sequentially from first step to last step of each revolution, wherein each step or a group of steps has an individual speed and an individual pause time between steps or a group of steps;

(c) the liquid flow, in the output of the pump, in measured in each step and pause; and (d) calculating or changing the speed of each step and duration of each pause, to have the desired flow function.

The algorithm can be used sequentially during the pump work, or can be used for calibration to obtain a revolution function—speed and time for each step and pause—and then use the obtained function to revolve the motor in further work.

According to another aspect of the present invention, there is provided a sensor unit for sensing the presence of gas cavities in a liquid flowing through a lumen of a flexible tube segment. The sensor comprises a transmitter unit having an arced transmitter plate with an apex extending along a line defining a first axis and a receiver unit having an arced receiver plate with an apex extending along a line defining a second axis. The two plates are preferably oppositely arced with their apexes facing one another defining a sensing space between them, the first and the second axes being essentially perpendicular to one another. Typically and preferably, the sensor is ultrasonic.

By second preferred embodiment, the tube extends through the sensing space such that each of the arced transmitter plate and the arced receiver plate contacts the tube.

By another preferred embodiment, the present invention includes communication capability enabling it to use any communication infrastructure to deliver information and receive commands.

By another aspect, there is provided a dripping sensor for sensing and counting the drips inside the drip chamber.

By another aspect, there is provided a sensor unit for a pump adapted for determining the pressure of a liquid flowing within a flexible tube segment. The sensor comprises a tube receiving space formed by walls engaging at least a portion of the tube while it is received within the space. Preferably, a sensing member projects into the space for determining deformation-resistance of the tube.

Preferably, the sensing member comprises a plunger associated with a strain gage. The tube receiving space is defined, by a preferred embodiment, between four walls defining a rectangular shape, and the plunger projects through one of the walls. By one specific design, the tube receiving space is defined between two or more arced surfaces.

Preferably, at a non-pressurized state of the tube, there remains a known clearance between the walls of the tube receiving space and the tube, whilst the tube is also deformed by the plunger at a non-pressurized state thereof.

In another aspect, the present invention provides a pump for propelling liquid through a lumen of a flexible tube segment. The pump includes a first tube-clamping member, a first set of tube squeezing members, a second tube-clamping member, a second set of tube squeezing members, wherein the members are arranged in a direction from upstream to downstream, a motor and a motor control in operative connection with the motor. The motor control provides energy input to the motor to drive the motor and receives feedback from the motor of motor function. The motor control includes a motor control protocol that controls the energy input to the motor based upon the feedback received from the motor. The motor control protocol causes a rapid increase in energy provided to the motor if motor feedback indicates an unusual load on the motor. The pump can also include a synchronizing device operably associated with the motor and the members. The synchronizing device is operable to activate the members in a sequential order such that fluid in the tube is displaced in a downstream direction.

Pumps and flow sets in connection with which the motors and motor controls of the present invention can be used are described, for example, in Published U.S. Patent Application Nos. 2002/0127114 A1 and 2002/0177821 A1, the disclosures of which are incorporated herein by reference. The motor control protocol of the motor control can, for example, increases the energy supplied to the motor in a predetermined manner for a predetermined period of time. If motor feedback indicates an unusual load on the motor at the end of this period of time the motor control protocol causes a rapid increase in energy provided to the motor.

The motor control protocol can first cause a decrease in energy provided to the motor before causing the rapid increase in energy. In one embodiment, the energy is decreased to a minimum level and then rapidly increased to a maximum level for a period of time.

The motor control protocol can repeat the decrease in energy and subsequent rapid increase in energy a predetermined number of times if motor feedback indicates continued abnormal function of the motor.

In another aspect, the present invention provides a motor and a motor control in operative connection with the motor, wherein the motor control provides energy input to the motor to drive the motor and receives feedback from the motor of motor function. The motor control includes a motor control protocol that controls the energy input to the motor based upon the feedback received from the motor. As described above, the motor control protocol causes a rapid increase in energy provided to the motor if motor feedback indicates an unusual load on the motor.

In still another aspect, the present invention provides a method of controlling a motor of a pump, including the steps: providing energy input to the motor to drive the motor; receiving feedback from the motor of motor function; controlling the energy input to the motor based upon the feedback received from the motor; and rapidly increasing the energy provided to the motor if motor feedback indicates an unusual load on the motor.

As described above, the energy provided to the motor can first be decreased before being rapidly increased. In one embodiment, the energy is decreased to a minimum level and then rapidly increased to a maximum level for a period of time.

The energy supplied to the motor can, for example, be increased in a predetermined manner for a predetermined period of time. If motor feedback indicates an unusual load on the motor at the end of this period of time, the energy provided to the motor is then rapidly increased.

If after an initial decrease in energy provided to the motor and subsequent rapid increase in energy provided to the motor, a decrease in energy and subsequent rapid increase in energy can be repeated a predetermined number of times if motor feedback indicates continued abnormal function of the motor.

The motor can, for example, be operated in an MR environment. During operation in and MR environment, the abnormal function of the motor can be a result of an MR magnetic field.

In one embodiment, energy provided to the motor is increased in steps of a preset increment of time during the predetermined period of time. The energy supplied to the motor can, for example, be increased to its maximum level in a single step if motor feedback indicates an unusual load on the motor at the end of the predetermined period of time (during which energy to the motor is relatively gradually increased as described above). As also described above, the energy provided to the motor can be decreased before being increased. In one embodiment, the energy is decreased to a minimum level and then increased to a maximum level in a single step. As also described above, after an initial decrease in energy provided to the motor and a subsequent increase in energy provided to the motor, a decrease in energy and subsequent increase in energy can be repeated a predetermined number of times if motor feedback indicates continued abnormal function of the motor.

BRIEF DESCRIPTION OF THE DRAWINGS

In order to understand the invention and to see how it may be carried out in practice, a preferred embodiment will now be described, by way of non-limiting examples only, with reference to the accompanying drawings, in which.

DETAILED DESCRIPTION

Figure 1:
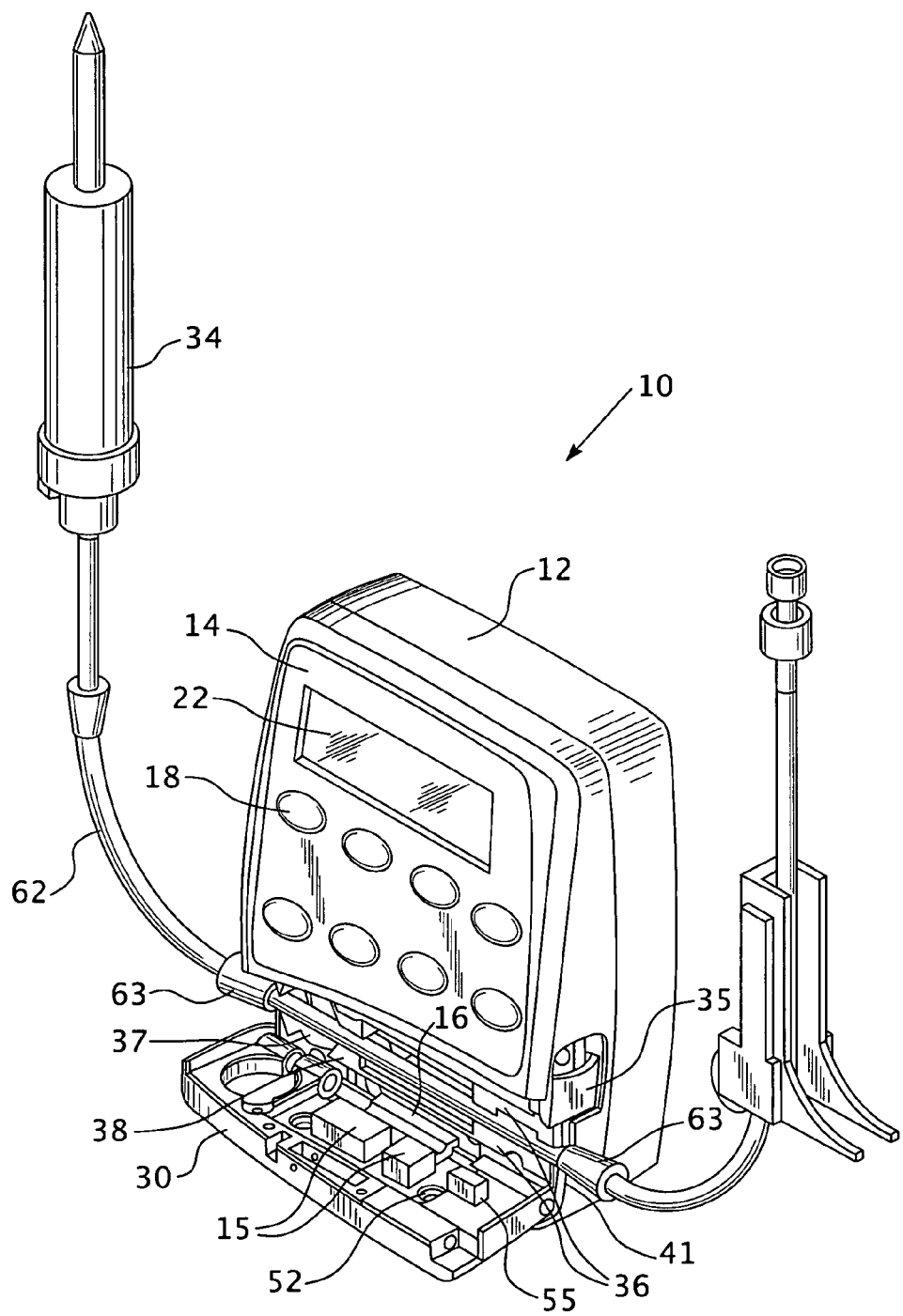
FIG. 1 is an isometric view of a pump in accordance with the present invention comprising a receptacle door being opened prior to engagement with a tube segment.

Reference is first made to FIG. 1, in which a piston pump (generally designated 10) is shown, comprising a housing 12, having a user interface unit 14 and a pumping assembly (generally designated 16). Typically, user interface 14 comprises a keypad 18, for input of data such as flow rate, flow time, etc., and to initiate or stop the pump, and a display 22.

The pumping assembly 16 comprises a door 30 pivotally engaged at pivots to a support structure of the pump (not shown). Door 30 comprises a release lever 35, a biasing spring (not shown) and an engaging hook portion 38 adapted for engagement with a corresponding lateral shoulder of a locking recess formed in the housing 12.

Door 30 carries also a counter member 15, which in the present embodiment is sprint biased by means of springs 52. The counter member 15 may be a rigid bar covered by a layer of flexible material, or it may also be made of a flexible material, e.g. a bar of silicon rubber, etc. The purpose of this counter member 15 will become apparent hereinafter.

The housing is formed with a receptacle 41 for receiving a segment—between two stoppers 63—of a flexible tube 62 of a flow set 34, such as of a drug administration set, etc. The receptacle 41 extends across the housing 12 between openings formed in the sidewalls of the housing 12. Receptacle 41 is also formed with two-well shaped portions and a major receptacle portion. It is further noted that the door 30 comprises a tube positioning extension 55 for depressing and positioning the tube 62 within the receptacle 41 at the openings of the housing. Furthermore, the receptacle may be provided with a micro switch (not shown) for generating a signal to the control unit of the pump, indicative of engagement of the pump with a segment of the tube. Suitable sensor means may also be provided to indicate proper closure of door 30. Two openings 37 are formed one in the door 30 and the other in the housing 12 to locate two parts of an air sensor. A pressure sensor 36 is located in the housing 12 between two sides of the tube 62.

Figure 2:
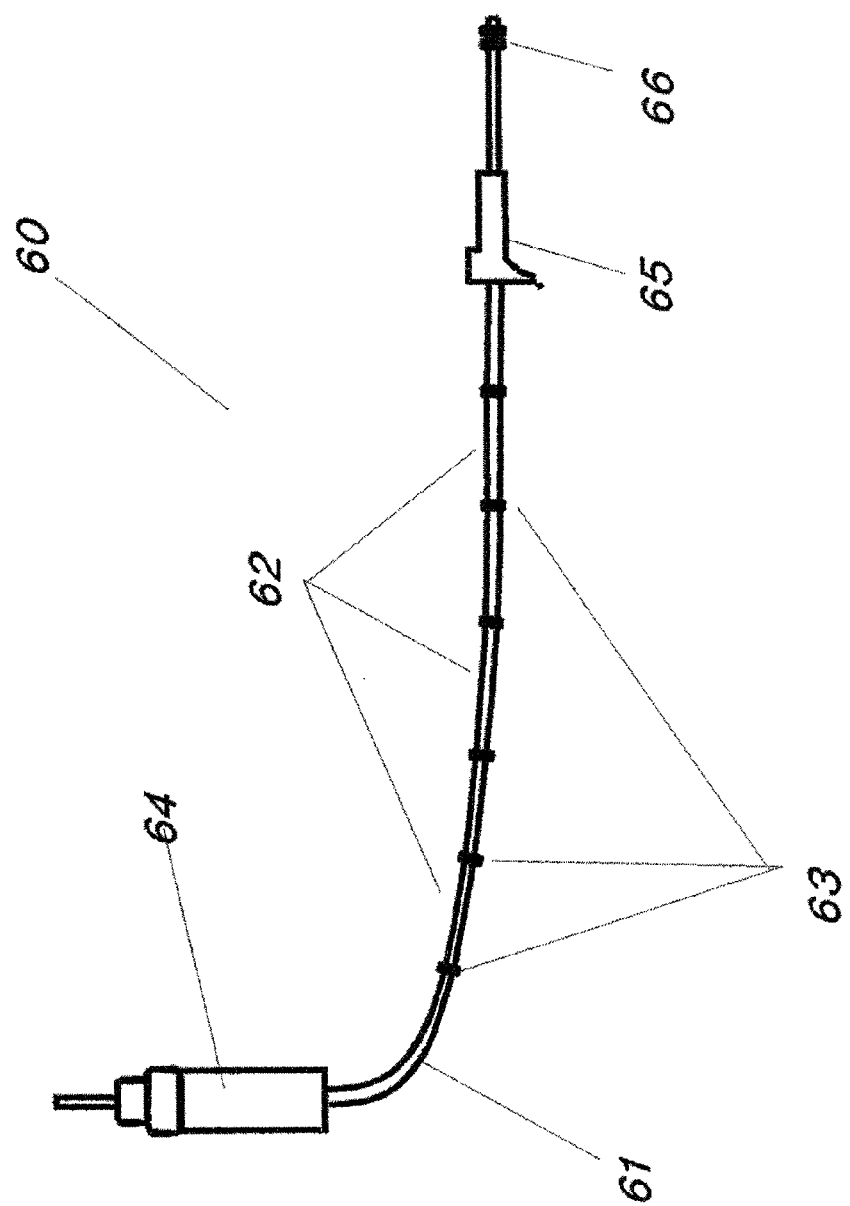
FIG. 2 is an illustration of a disposal flow set.
Figure 3A:
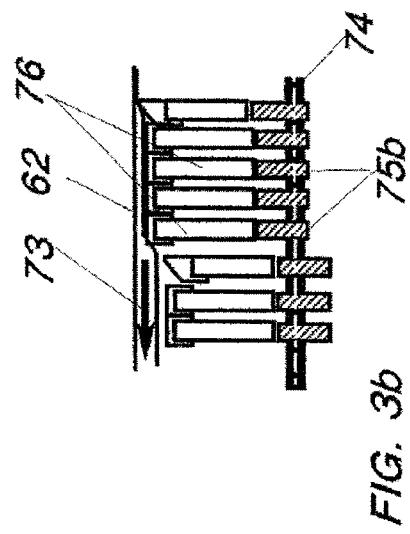
FIGS. 3a–3d show, in isolation, the piston mechanism, in continuous consecutive phases of the pump's operation.
Figure 3B:
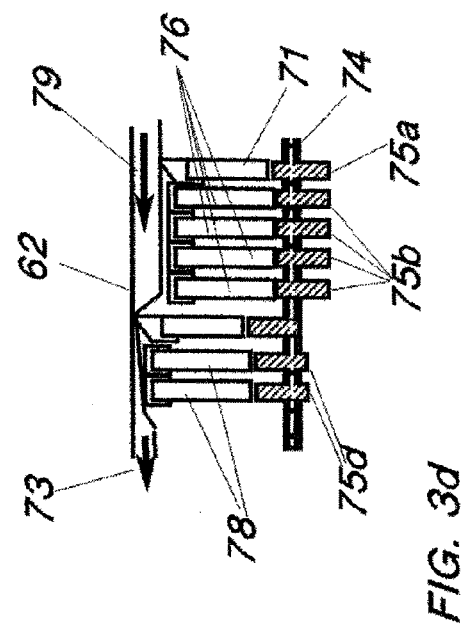
Figure 3C:
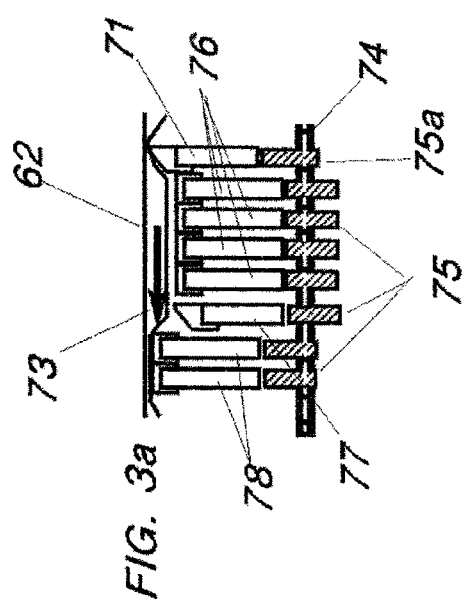
Figure 3D:
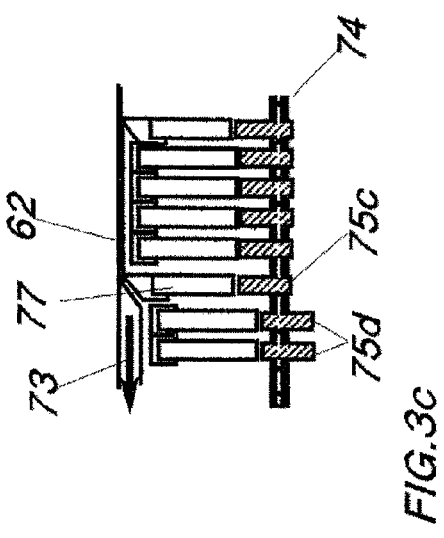

FIG. 2 illustrates a disposal flow set for use with the pump in order to administer a liquid. The flow set 60 includes an administration tube 61, which is separated into a number of pumping segments 62 wherein each segment is bordered by two stoppers 63. The stoppers 63 are used to locate one of the pumping segments in the pump, and when a segment loses its flexibility it can replaced by another segment. The flow set 60 includes a dripping chamber 64 that can be used for, inter alia, sensing and counting the drops passing through the chamber using a drip sensor (not shown). The flow set 60 includes a valve 65 and a connector 66 to connect the set to a patient.

FIGS. 3a–3d show, in isolation, the piston mechanism, in continuous consecutive phases of the pump's operation. The pump includes a first clamping member 71, a first set of squeezing members 76, a second clamping member 77, a second set of squeezing members 78, and an axis 74 with a number of eccentric cams 75 installed thereon to elevate and to lower each member according to the pumping sequence in order to clamp and squeeze a tube segment 62 to administer the liquid flow 73 from right to left.

In a first step, (FIG. 3a) the axis 74, with the eccentric cams 75, is revolved to a position that elevates the first clamping member 71 by an associated cam 75a, whereby the first clamping member clamps the right end of the tube segment 62. In a further stage of FIG. 3b, the axis 74 continues its revolution and the first set of squeezing members are elevated by associated cams 75b. The squeezing members 76 squeeze the tube segment 62 and force the liquid 73 to move left. In the next step (FIG. 3c), by the continuation of the revolution of the axis 74, the second clamping member 77 is elevated by an associated cam 75c and clamps the tube segment 62 in the left end of the squeezed area. Meanwhile, the second squeezing set 78 is still elevated from the previous sequence, by the associated cams 75d, and starts to move down to ensure the continued flow of the liquid 73.

In the last sequential step (FIG. 3d), by the continuation of the axis 74 to revolve, the second set of squeezing members 78 are finished elevating and, in the meantime, the first set of squeezing members 76 and the first clamping member 71 are lowered by the associated cams 75a and 75b. While the remaining liquid 73 is pushed to the left, a new liquid 79 from a container (not shown) fills the right released part of the tube segment 62, ready for the next sequence of the pump when the second set of squeezing members 78 and the second clamping member 77 are lowered and the first clamping member 71 is elevated.

For best performance, preferably the squeezing size area of the first set of squeezing members 76 is about double the size of the squeezing size area of the second set of squeezing members 78, so as to ensure continuous propagation of liquid in a downward direction, where the volume of liquid received within the tube segment corresponding with the area of tube squeezing members 76 serves as a reservoir of liquid.

The cams are angularly diverted such that at least one or more of the cam followers constitute the first tube clamping member, one or more other cam followers constitute the second tube clamping member, several other cam followers arranged in the same orientation constitute the first set of tube squeezing members, and several other cam followers arranged in the same orientation constitute the second set of tube squeezing members.

Different parameters are maintained similar to the previous embodiment, e.g., the tube blocking cam followers engage the respective tube segment so as to essentially block the tube's lumen, whilst the tube squeezing cam followers engage the respective tube segment to only partially squeeze the tube's lumen. This may be achieved by differently forming the tube-engaging surface of the cam followers, or by shortening their lengths or by different forms of the cams.

Figure 4:
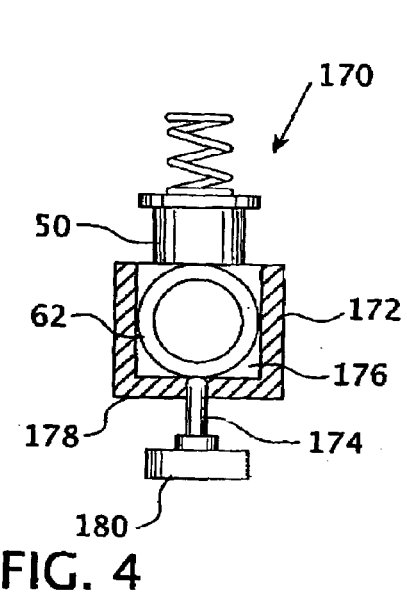
FIG. 4 is a sectional view of a pressure-sensing unit for incorporation in a pump of the aforementioned type.

In FIG. 4 of the drawings, there is illustrated a pressure sensing device 170 incorporated into the pump in accordance with the present invention, or other liquid administrating pumps, and is suitable for placing within one of the cavities 46 or 48 formed in the housing 12. The sensor unit 170 comprises a U-like receptacle 172 dimensioned so as to comfortably accommodate tube 62, with a suitable counter member 50 closing the structure from above. A plunger 174 projects into the space 176 confined within the U-like receptacle 172 through a suitable opening at a bottom wall thereof 178 and is associated with a pressure sensing gauge 180, e.g. a piezoelectric gauge, string gauge, etc., for detecting pressure applied thereto by the tube 62, depending on its internal pressure applied by the liquid flowing through its lumen.

The arrangement of the sensor 170 ensures that local deformation of the tube is converted into terms of pressure without influence of overall deformation of the tube caused by the internal pressure of the liquid, this owing to the support walls of structure 172 preventing undesired deformation of the tube.

Figure 5:
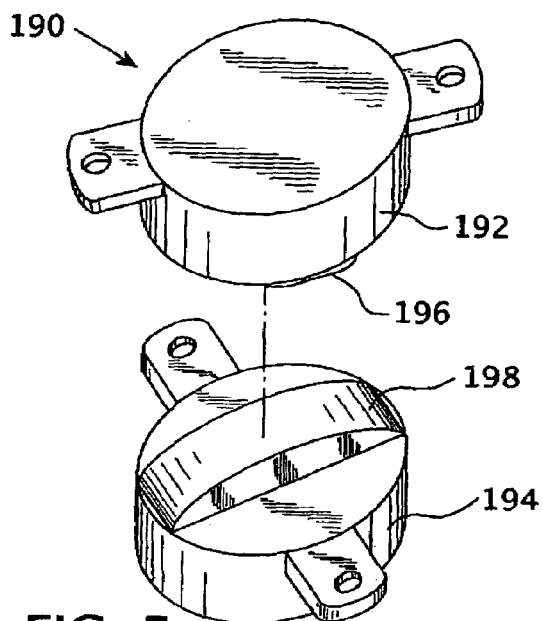
FIG. 5 is a perspective, exploded view of a gas detection sensor for use in a pump of the aforementioned type.
Figure 6A:
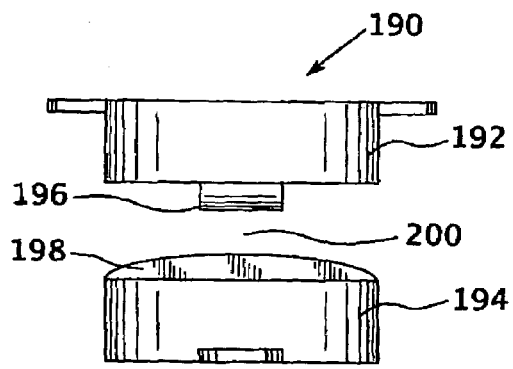
FIGS. 6A and 6B are side views of the device seen in FIG. 4 rotated by 90'.
Figure 6B:
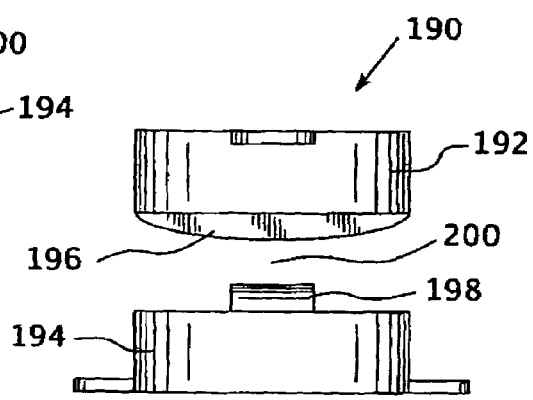

FIGS. 5 and 6 illustrate a sensor for detecting the presence of gas, typically air, flowing within the liquid carrying tube. The device (generally designated 190) is suitable for insertion within one of the cavities 46 or 48 of housing 12 and comprises a transmitter unit 192 having an arced transmitter plate 196 and a receiver unit 194 having an arced receiver plate 198, with the two plates 196 and 198 being oppositely arced with their apexes facing one another defining between them a sensing space 200 (FIGS. 6A and 6B). In order to achieve sensing focus, the two plates 196 and 198 are preferably perpendicular to each other. Typically, the sensor is ultrasonic.

The arrangement is such that the entire cross-section of the tube is covered by the ultrasonic waves, thereby any air cavities, even if significantly small with respect to the cross-section of the tube, and even if not flowing axially centered within the tube, are detected.

In several embodiments, the pumps of the present invention are particularly well suited for use in a magnetic resonance environment. In general, most of the pump components can be readily fabricated from MR compatible materials as discussed, for example, in Published U.S. Patent Application No. 2003/0014035 A1, the disclosure of which is incorporated herein by reference. As used herein, the term "MR compatible" refers generally to materials and devices that do not substantially adversely affect the magnetic resonance imager and which are not substantially adversely affected by the magnetic resonance imager.

Magnetic resonance imaging (MRI) is used to image the body in a non-invasive manner. There are three types of electromagnetic fields used in MRI: a main static magnetic field (having field strengths from, for example, approximately 0.2 to several Tesla) which is generally homogeneous in the imaged volume; time varying magnetic gradient fields ($G_x$, $G_y$ and $G_z$), which have different orientations and operate at frequencies on the order of 1 kHz; and a radio frequency ("RF"; having, for example a frequency of approximately 63.87 MHz for a 1.5 Tesla static field strength).

MRI is often scheduled to image patients that may be attached to other types of equipment, such as ventilators, infusion pumps, or other devices. However, most currently available devices fail to operate correctly in the high magnetic fields generated in MRI, create undesirable artifacts in the resultant image, and/or contain ferrous materials that are susceptible to magnetic fields. As a result, there are a substantial number of MRI procedures that are severely hampered, delayed or canceled because the patient cannot be connected to the needed equipment during the MRI procedure. A review of issues related to the compatibility of various equipment in an MRI environment is set forth in Keeler, E. K. et al., "Accessory Equipment Considerations with Respect to MRI Compatibility," *JMRI*, 8, 1 (1998), the disclosure of which is incorporated herein by reference. See also, Lemieux, L. et al., "Recording of EEG During MRI Experiments: Patient Safety," *MRM* 38, 943 (1997); and "A Primer on Medical Device Interactions with Magnetic Resonance Imaging Systems," U.S Food and Drug Administration—Center for Devices and Radiological Health (Feb. 7, 1997), the disclosures of which are incorporated herein by reference.

In general, many devices, including but not limited to infusion pumps, that contain electric actuators such as DC brush motors, step motors, brushless DC motors or other wound coil motors and solenoids, often fail in a strong magnetic field as a result of damage to internal permanent magnets. Moreover, currents induced within the field windings of such devices from electromagnetic fields can cause overheating and potential damage to the windings and any connected electronic circuitry. The MRI magnetic field can also interfere with the device created magnetic field and prevent accurate operation.

Furthermore, differences in magnetic permeability of materials within the actuator and eddy currents induced within actuator windings can affect the homogeneity or uniformity of the MRI magnetic field, generating image artifacts. Actuators that use mechanical commutation, such as DC brush motors, can also generate radio frequency energy during switching which can induce unwanted artifacts upon the acquired MRI images. Shielding of actuator such as electric motors reduces the adverse effect MRI magnetic fields.

At low flow rates, it has been discovered that even with shielding of certain pump components the magnetic field of the MRI device can adversely affect the operation of pumps, including the pumps of the present invention. In general, the pumps of the present invention require the highest power input during starting of the motor. Substantial increases in power consumption have been measured over short periods of time (a few milliseconds) under such conditions. The problem is more significant at very low infusion rates, as the motor is stopped and restarted frequently during low infusion rates. In the MRI environment (that is, in the vicinity of a magnetic resonance imaging device), the MR magnet exacerbates the problem by loading the motor and motor gearing during the relatively short starting period.

Initially, the motor and motor gear (if metallic) is preferably shielded by, for example, inserting a ferromagnetic shield or shields over the motor and motor gear. DC motors are typically shielded, but the motor gear is left unshielded. If the gear(s) are made of metal, the gears will become magnetized in an MRI environment, and the gear shafts will be deformed, forcing them out of balance. Furthermore, operation of an unshielded motor gear in an MR environment over time causes damage to the unshielded motor gear and current draw will rise substantially. Eventually, the pump will fail. Thus, any metallic motor gear to be used in an MR environment is preferably shielded as described above.

Figure 7:
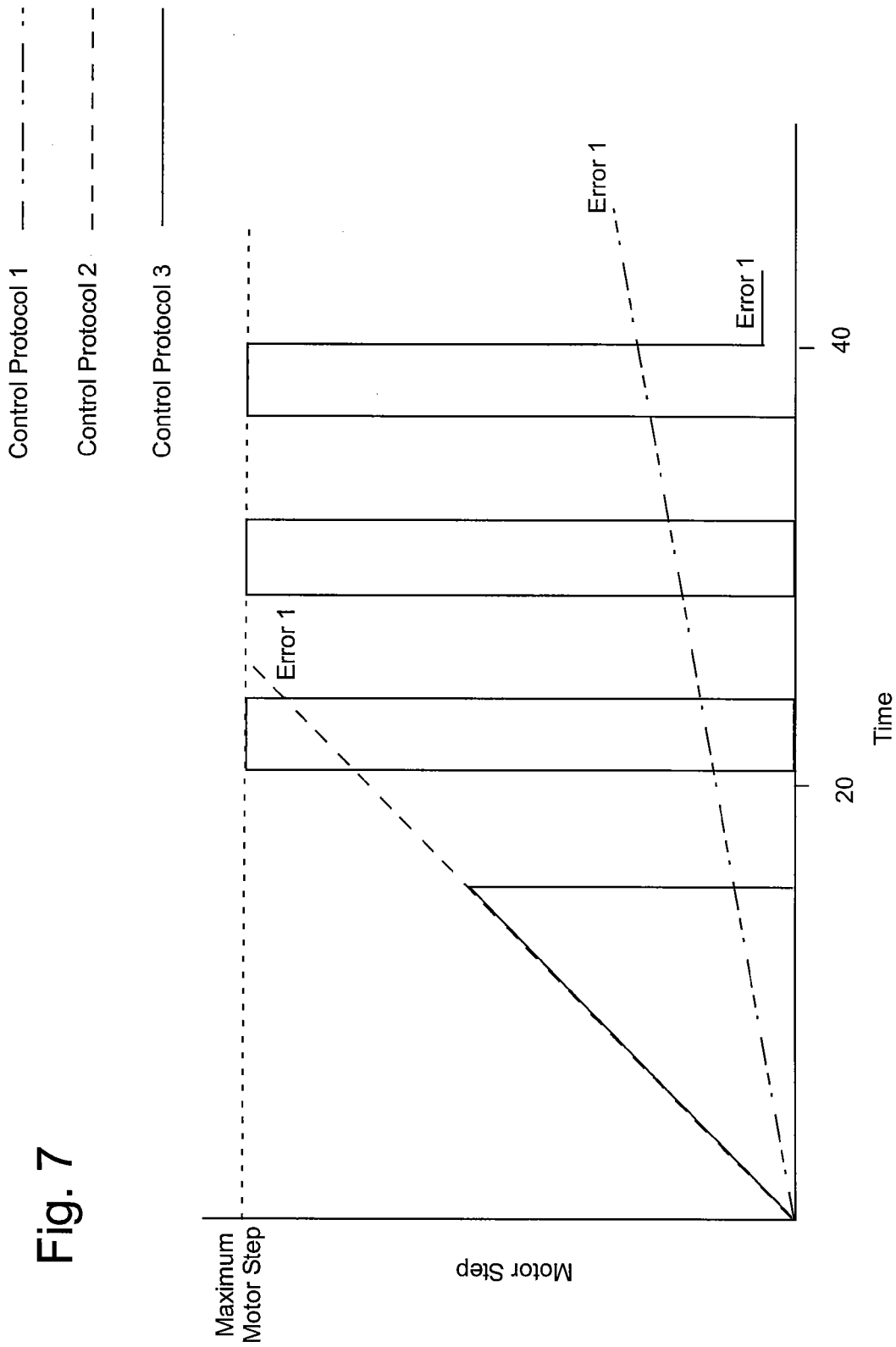
FIG. 7 is a graphical illustration of several pump control protocols for use with the pumps of the present invention.

In addition to shielding metallic motor gears, it has been discovered that certain motor control protocols as illustrated, for example, in FIG. 7 substantially reduce or eliminate the occurrence of pump errors or malfunctions during operation in an MR environment. In one embodiment, a motor drive control protocol of the present invention was based on steps in which each step is change (increase or decrease) in voltage (or current) as compared to a previous step. Using feedback control, the motor steps input to the motor are a function of a predetermined control protocol and a measured motor function or output.

Figure 8:
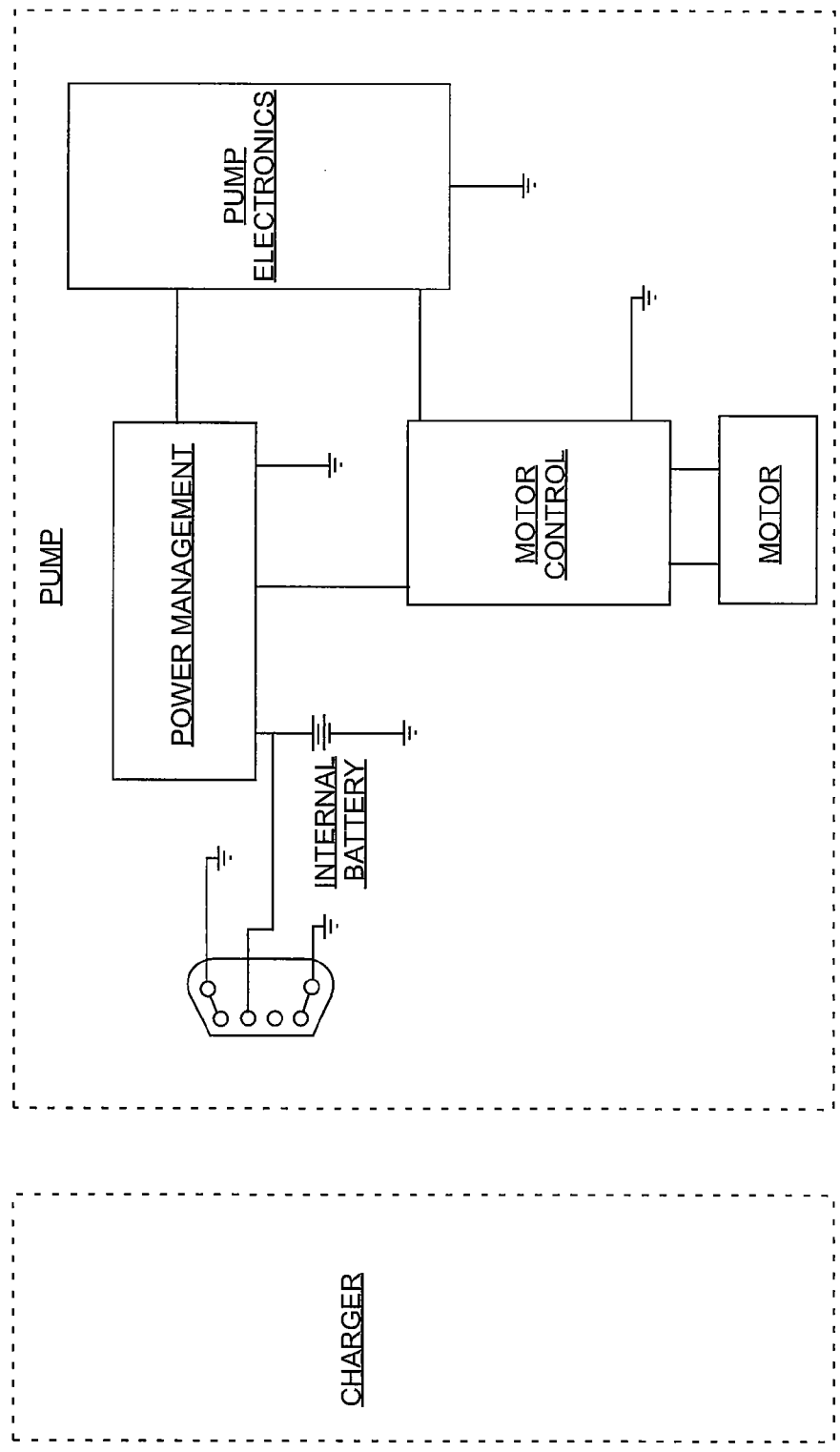
FIG. 8 is a block diagram of one embodiment of a pump of the present invention and a battery charger for use therewith.

In general, energy applied to the motor is preferably increased under a control protocol as necessary to provide adequate power to perform a task, but providing power in excess of the required power is preferably avoided to assure relatively smooth and continuous turning of the motor. Such a control protocol minimizes noise and pulsation in the flow created by the pump. Preferably, motor speed or spin rate is monitored (for example, via position encoding as known in the art) and feedback is provided to a motor control (see FIG. 8). The motor control can, for example, include a microprocessor including a memory in which a motor control protocol or algorithm is stored. Under one embodiment of a control protocol, energy supplied to the motor can, for example, be increased or decreased (for example, in small steps) depending upon the desired motor speed (determined by a desired flow rate) and measured motor speed until an "optimal" energy input as described above is achieved. During normal pump operation, increases or decreases in motor steps are limited in time. That time determines the shape or slope of the motor curve (time vs. voltage (motor steps)).

Under a first motor control protocol or motor control protocol 1, as illustrated in FIG. 7, energy to the motor was increased according to a predetermined motor curve. However, errors occurred often during operation in an MR environment as the load placed on the motor by the MR magnetic field(s) caused the motor to not reach full output power in a designated time period (for example, 40 time units wherein each time unit is 0.25 seconds). In one embodiment of motor control protocol 1, energy/power was increased or motor step was increased in increments of 0.25 msec when the motor was instructed by the motor control processor to move in the case that the previous step was not adequate to cause motor movement. An error (designated Error 1) occurred when the motor failed to move (turn) in the predetermined time frame of 40 time units. A motor curve for motor control protocol 1 resulting in Error 1 is illustrated in FIG. 7. Under a second motor control protocol or motor control protocol 2, the slope of the motor curve was increased to increase energy supplied to the motor over a shorter period of time. Under motor control protocol 2, the maximum motor step is supplied to the motor after a shorter period of time than under motor control protocol 1. Reducing the time required for the motor to reach maximum motor step was found to decrease the frequency of Error 1, but did not eliminate the error in all cases. In that regard, occasionally the motor failed to turn even after maximum motor step (maximum energy input) was reached for a set period of time.

Under a third motor control protocol or motor control protocol 3, the motor steps were increased to initially follow the general curve of motor protocol 2 for a predetermined period of time (for example, ⅓ of 40 time units in the embodiment of FIG. 7). If the motor is operating normally, the motor will reach a suitable spin rate in the predetermined time and no change from the motor curve of motor control protocol 2 will occur. However, if the motor fails to turn, the energy supplied to the motor is preferably first decreased (for example, to the minimum motor step) and then rapidly increased (for example, to the maximum motor step) for a period of time (for example, approximately 1 second) to develop additional inertia to overcome the resistance to turning.

The rapid increase in energy applied to the motor occurs at a rate substantially faster than the gradual increase in energy applied in the initial phase of motor control protocol 3. In one embodiment, the energy was increased to maximum level in one step of 0.25 msec. The difference can be analogized to applying a gradually increasing force to a stuck door (the initial phase of motor control protocol 3) compared to stepping away from the door and running into it with a sudden burst of force (the latter phase of motor control protocol 3). Under motor control protocol 3, the pressure on tubing 62 is first released when the energy supplied to the motor is decreased. Resistance to deformation of tubing 62 may cause the pump mechanism (as described above) to reverse or decrease a few intervals.

In one embodiment of motor control protocol 3, the energy to the motor was decreased to its minimum level or step and subsequently increased to its maximum level or step in a single step after about 0.25 seconds. This process is repeated a preset number of times (three times in the embodiment of FIG. 7). If the motor does not turn after the present number of such "jump" "knock" cycles, Error 1 is indicated.

As described above, the motor curve of motor control protocol 3 preferably initially follows the general path of motor control protocol 2 to, for example, minimize noise and pulsation in flow. Only if the motor does not turn or otherwise exhibits abnormal behavior associated, for example, with increased or abnormal loads resulting from MR magnetic field(s) does the motor control cause the relatively rapid decrease(s) and increase(s) in motor energy described above. In addition to increasing noise and pulsation, such "jumps" or "knocks" can be damaging to the motor if repeated often. The rapid decreases and increases of motor energy associated with abnormal motor response are thus preferably applied only in cases of abnormal motor response (for example, failure to turn) and are preferably applied for only a brief period (for example, a portion of a second) to overcome an unusual load.

The foregoing description and accompanying drawings set forth the preferred embodiments of the invention at the present time. Various modifications, additions and alternative designs will, of course, become apparent to those skilled in the art in light of the foregoing teachings without departing from the scope of the disclosed invention. The scope of the invention is indicated by the following claims rather than by the foregoing description. All changes and variations that come within the meaning and range of equivalency of the claims are to be embraced within their scope.

The invention claimed is:

1. A pump for propelling liquid through a lumen of a flexible tube segment, the pump comprising:
   a first tube-clamping member;
   a first set of tube squeezing members;
   a second tube-clamping member;
   a second set of tube squeezing members, said members arranged in a direction from upstream to downstream;
   a motor;
   a motor control in operative connection with the motor, the motor control providing energy to the motor to drive the motor and receiving feedback from the motor of motor function, the motor control comprising a motor control protocol that controls the energy to the motor based upon the feedback received from the motor, the motor control protocol causing an impulse increase in energy provided to the motor if motor feedback indicates a stall load on the motor; and a synchronizing device operably associated with the motor and said members, the synchronizing device operable to activate said members in a sequential order such that fluid in the tube is displaced in a downstream direction.

2. The pump of claim 1 wherein the motor control protocol first causes a decrease in energy provided to the motor before causing the impulse increase in energy.

3. The pump of claim 2 wherein the energy is decreased to a minimum level and then impulse increased to a maximum level for a period of time.

4. The pump of claim 1 wherein the motor control protocol the motor control increases the energy supplied to the motor in a predetermined manner for a predetermined period of time, and if motor feedback indicates a stall load on the motor at the end of this period of time the motor control protocol causes an impulse increase in energy provided to the motor.

5. The pump of claim 4 wherein the motor control protocol first causes a decrease in energy provided to the motor before causing the rapid increase in energy.

6. The pump of claim 5 wherein the energy is decreased to a minimum level and then impulse increased to a maximum level for a period of time.

7. The pump of claim 5 wherein the motor control protocol repeats the decrease in energy and subsequent impulse increase in energy a predetermined number of times if motor feedback indicates continued abnormal function of the motor.

8. The pump of claim 6 wherein the motor control protocol repeats the decrease in energy to the minimum level and subsequent impulse increase in energy to the maximum level a predetermined number of times if motor feedback indicates continued abnormal function of the motor.

9. A pump comprising a motor and a motor control in operative connection with the motor, the motor control providing energy to the motor to drive the motor and receiving feedback from the motor of motor function, the motor control comprising a motor control protocol that controls the energy to the motor based upon the feedback received from the motor, the motor control protocol causing a rapid increase in energy provided to the motor if motor feedback indicates a stall load on the motor, and the motor control protocol first causes a decrease in energy provided to the motor before causing the impulse increase in energy.

10. The pump of claim 9, wherein the energy is decrease to a minimum level and then impulse increases to a maximum level for a period of time.

11. The pump of claim 9 wherein the motor control protocol of the motor control increases the energy supplied to the motor in a predetermined manner for a predetermined period of time, if motor feedback indicates a stall load on the motor at the end of this period of time the motor control protocol causes a rapid increase in energy provided to the motor.

12. The pump of claim 9 wherein the motor control protocol repeats the decrease in energy and subsequent impulse increase in energy a predetermined number of times if motor feedback indicates continued abnormal function of the motor.

13. The pump of claim 10 wherein the motor control protocol repeats the decrease in energy to the minimum level and subsequent impulse increase in energy to the maximum level a predetermined number of times if motor feedback indicates continued abnormal function of the motor.

* * * * *